US012151114B2

(12) United States Patent
English et al.

(10) Patent No.: US 12,151,114 B2
(45) Date of Patent: *Nov. 26, 2024

(54) AUTOMATIC LEAD LOCK FOR AN IMPLANTABLE MEDICAL DEVICE

(71) Applicant: Cardiac Pacemakers, Inc., St. Paul, MN (US)

(72) Inventors: James M. English, Cahir (IE); Moira B. Sweeney, St. Paul, MN (US); Trey H. Achterhoff, Arden Hills, MN (US); Benjamin J. Haasl, Forest Lake, MN (US); Robert A. Jones, Lake Elmo, MN (US); Daniel J. Foster, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/327,548

(22) Filed: Jun. 1, 2023

(65) Prior Publication Data

US 2023/0302284 A1 Sep. 28, 2023

Related U.S. Application Data

(63) Continuation of application No. 17/412,796, filed on Aug. 26, 2021, now Pat. No. 11,712,570.

(60) Provisional application No. 63/070,469, filed on Aug. 26, 2020.

(51) Int. Cl.
*A61N 1/375* (2006.01)

(52) U.S. Cl.
CPC ........ *A61N 1/3752* (2013.01); *A61N 1/37512* (2017.08)

(58) Field of Classification Search
None
See application file for complete search history.

(56) References Cited

U.S. PATENT DOCUMENTS

| 4,112,953 A | 9/1978 | Shanker et al. |
| 4,860,750 A | 8/1989 | Frey et al. |
| (Continued) | | |

FOREIGN PATENT DOCUMENTS

| EP | 0786269 A1 | 7/1997 |
| EP | 0900577 A1 | 3/1999 |
| EP | 0930913 | 7/1999 |

OTHER PUBLICATIONS

International Search Report and Written Opinion issued in PCT/US2020/052614, mailed Dec. 16, 2020, 14 pages.

(Continued)

*Primary Examiner* — Erica S Lee
(74) *Attorney, Agent, or Firm* — Nelson Mullins Riley & Scarbourough, LLP (57) ABSTRACT

Disclosed herein is an implantable medical device including a housing, a header, a connector port, and a collet assembly. The header can be arranged with the housing. The connector port can be arranged within the header and configured to couple an implantable lead to the header. The collet assembly can be arranged within the connector port and configured to frictionally engage a portion of the implantable lead and to secure the implantable lead with the header in response to insertion of the portion of the implantable lead into the connector port.

20 Claims, 6 Drawing Sheets

(56) References Cited

U.S. PATENT DOCUMENTS

| | | | | |
|---|---|---|---|---|
| 5,069,209 A | * | 12/1991 | Posin | H01R 13/187 |
| | | | | 439/837 |
| 5,413,595 A | | 5/1995 | Stutz | |
| 5,489,225 A | * | 2/1996 | Julian | H01R 4/5025 |
| | | | | 439/837 |
| 5,545,188 A | * | 8/1996 | Bradshaw | A61N 1/3752 |
| | | | | 607/37 |
| 5,707,399 A | | 1/1998 | Killander et al. | |
| 5,807,144 A | | 9/1998 | Sivard | |
| 7,035,689 B1 | | 4/2006 | Hawkins et al. | |
| 7,697,989 B1 | | 4/2010 | Lim et al. | |
| 8,108,045 B2 | | 1/2012 | Biggs, Jr. et al. | |
| 2010/0197174 A1 | | 8/2010 | Lahti et al. | |
| 2016/0375255 A1 | | 12/2016 | Janzig | |
| 2018/0200511 A1 | | 7/2018 | Ramesh et al. | |

OTHER PUBLICATIONS

International Search Report and Written Opinion received for PCT Patent Application No. PCT/US2021/047707, mailed on Dec. 20, 2021, 10 pages.

* cited by examiner

AUTOMATIC LEAD LOCK FOR AN IMPLANTABLE MEDICAL DEVICE

CROSS REFERENCE TO RELATED APPLICATION

This application is a continuation of U.S. patent application Ser. No. 17/412,796, filed Aug. 26, 2021, now U.S. Pat. No. 11,712,570 which claims priority to Provisional Application No. 63/070,469, filed Aug. 26, 2020, both of which are herein incorporated by reference in their entireties.

TECHNICAL FIELD

The present disclosure relates to an implantable system having an implantable lead and a connector port. More specifically, the disclosure relates to releasably securing of the implantable lead within the connector port.

BACKGROUND

Implantable medical systems may include an implantable lead assembly and an implantable pulse generator connected with the implantable lead assembly. Further, a header of the implantable pulse generator generally includes corresponding connector ports to effectively couple the lead assembly with the implantable pulse generator. A proper connection between the implantable leads and the corresponding connector ports is required to allow proper functioning of the implantable system. The lead assembly and the implantable pulse generator are to remain connected after implantation to ensure desired functionality.

SUMMARY

According to embodiments of the present disclosure, in a first example, an implantable medical device including a housing, a header, a connector port, and a collet assembly. The header can be arranged with the housing. The connector port can be arranged within the header and configured to couple an implantable lead to the header. The collet assembly can be arranged within the connector port and configured to frictionally engage a portion of the implantable lead and to secure the implantable lead with the header in response to insertion of the portion of the implantable lead into the connector port.

In some such examples, the collet assembly or a portion thereof includes an angled outer circumference, an inner surface of the connector port or a portion thereof includes an angled inner circumference, or both. The collet assembly can include one or more bearings arranged about a circumference of the collet assembly and configured to contact an inner surface of the connector port.

In some such examples, the collet assembly can be configured to clamp down on the portion of the implantable lead in response to insertion of the portion of the implantable lead into the connector port. The collet assembly can be split at a portion of a circumference thereof.

In another example, an implantable medical device comprising can include a housing, a header, a connector port, and a collet assembly. The header can be arranged with the housing. The connector port can be arranged within the header and configured to couple an implantable lead to the header. The collet assembly can be arranged within the connector port and configured to clamp against a portion of the implantable lead and to secure the implantable lead with the header in response to insertion of the portion of the implantable lead into the connector port.

In another example, an implantable medical device comprising can include a housing, a header, a connector port, and a collet assembly. The header can be arranged with the housing. The connector port can be arranged within the header and configured to couple an implantable lead to the header. The collet assembly including one or more bearings arranged about a circumference of the collet assembly, the one or more bearings configured to contact an inner surface of the connector port arranged within the connector port and configured to frictionally engage a portion of the implantable lead and to secure the implantable lead with the header in response to insertion of the portion of the implantable lead into the connector port.

In another example, a method of coupling an implantable lead to an implantable medical device. The method can include coupling the implantable lead to the implantable medical device by moving the implantable lead in a first direction into a connector port arranged within a header of the implantable medical device. The method can include engaging and securing a portion of the implantable lead with a collet assembly arranged within the connector port in response to insertion of the portion of the implantable lead into the connector port.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
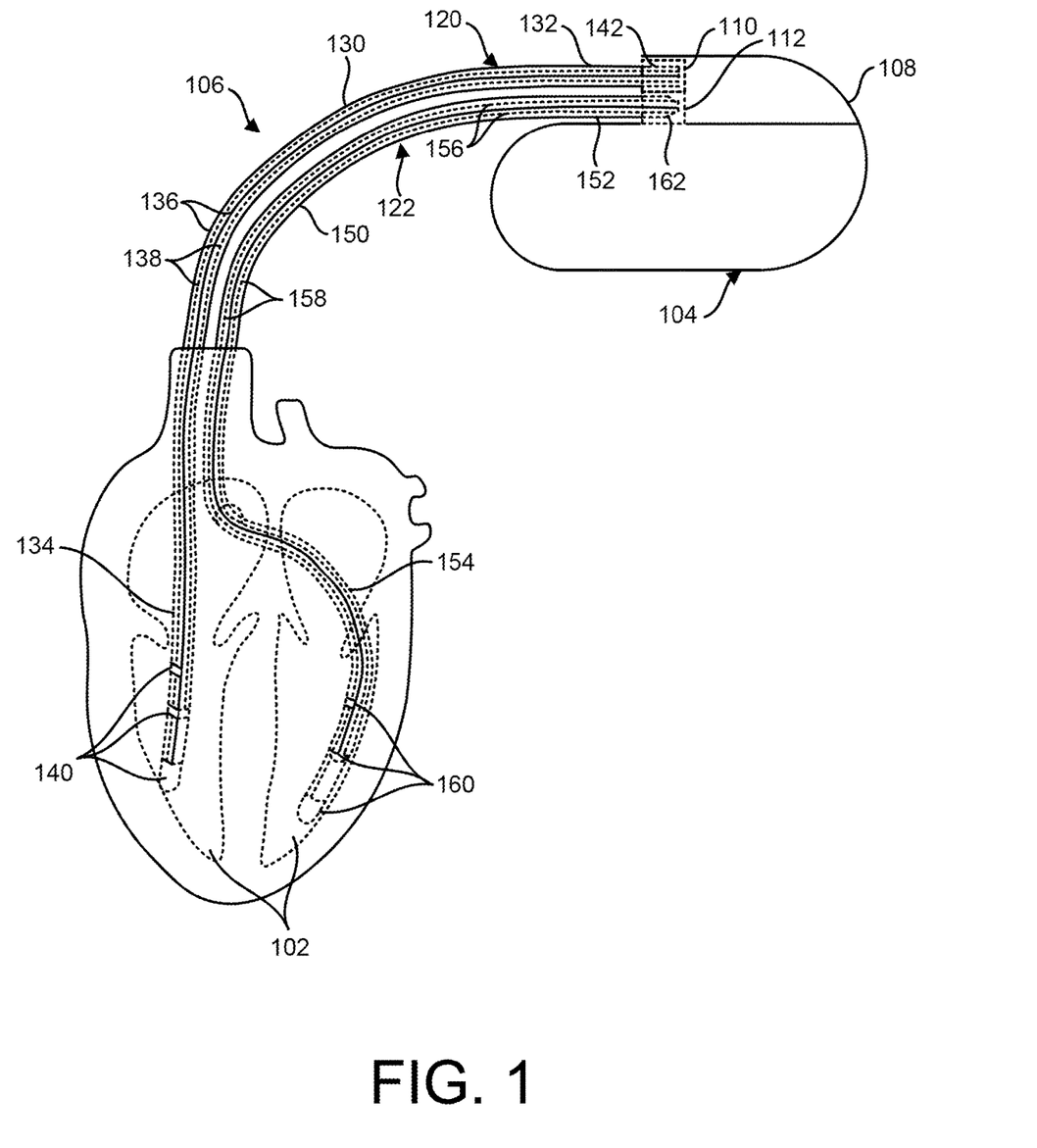
FIG. 1 is an illustration of an example implantable system for stimulating a target location on or within the heart, in accordance with various aspects of the present disclosure.

FIG. 1 is a schematic illustration of an implantable system 100 for stimulating a target location 102 on or within the heart. As shown, the implantable system 100 includes an implantable medical device (IMD) 104 and an implantable lead assembly 106 connected to the IMD 104. In various embodiments, the IMD 104 is an implantable pulse generator adapted to generate electrical signals to be delivered to the target location 102 for pacing and/or for sensing electrical activity at a location on or within the heart. The IMD 104 can include microprocessors to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia. In other instances, the implantable system 100 can also be suitable for use with implantable electrical stimulators, such as, but not limited to, neuro-stimulators, skeletal stimulators, central nervous system stimulators, or stimulators for the treatment of pain.

The IMD 104 may include one or more connector ports 110, 112. In certain instances, the IMD (e.g., pulse generator 104) includes a header 108 with the connector port(s) 110, 112. As shown, for example, the header 108 includes a first connector port 110 and a second connector port 112. In addition, the implantable lead assembly 106 includes a first implantable lead 120 connected to the first connector port 110 and a second implantable lead 122 connected to the second connector port 112. In some instances, the implantable lead assembly 106 may also include a third implantable lead (not shown) and the header 108 may include a corresponding third connector port (not shown).

Figure 5:
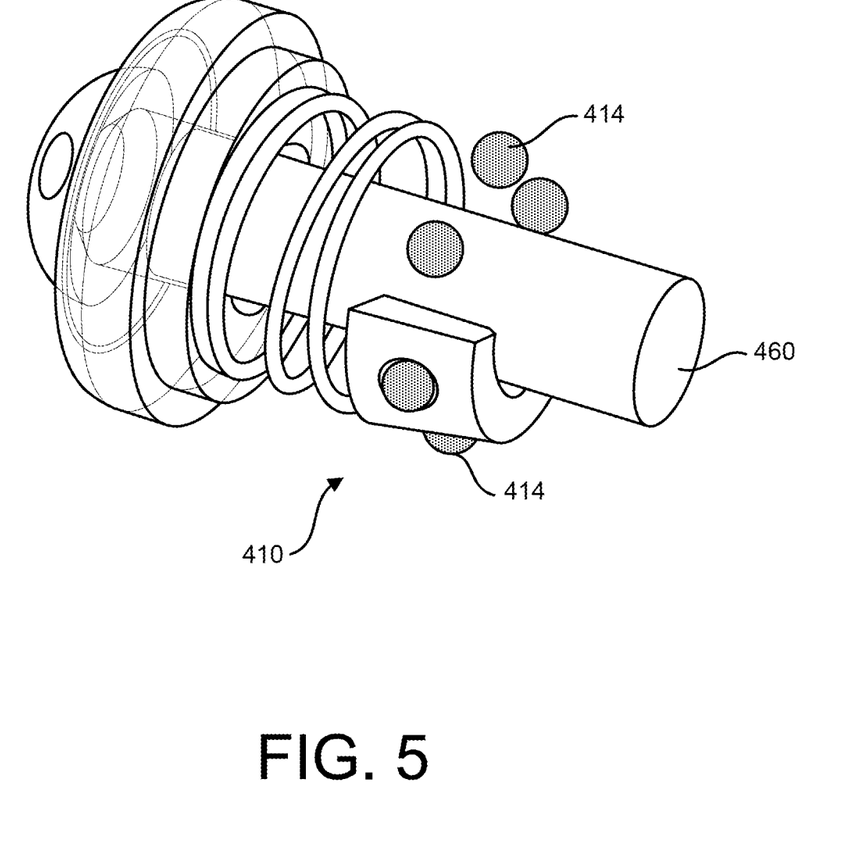
FIG. 5 is a perspective exploded view of an illustration of another example connector port and collet assembly, in accordance with various aspects of the present disclosure.
Figure 6:
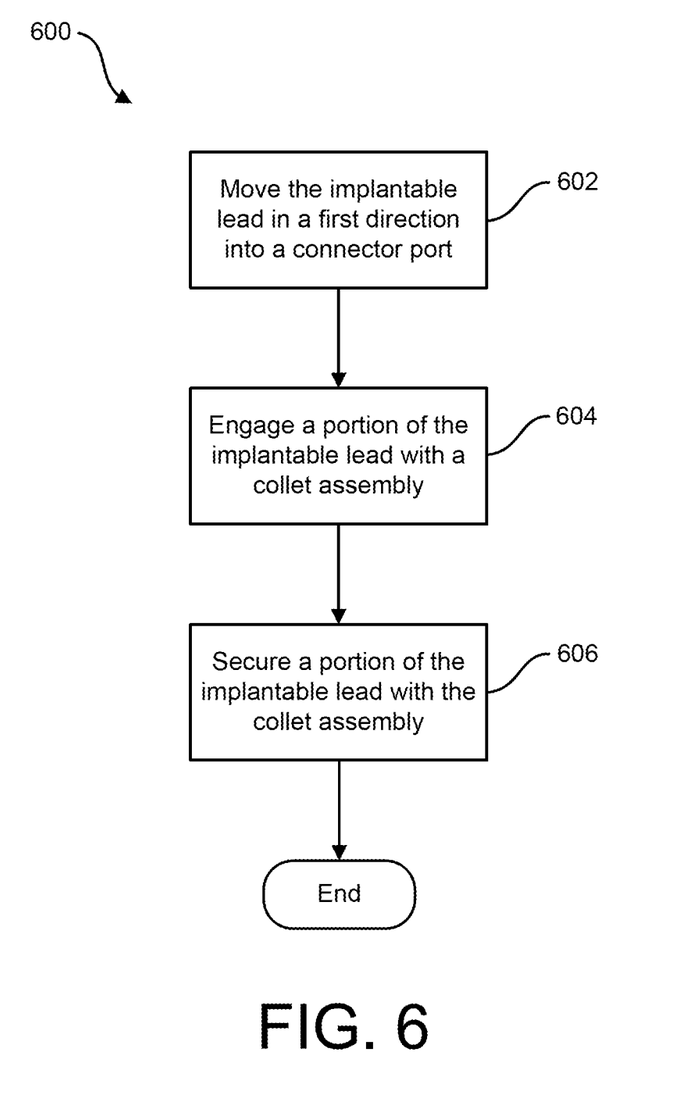
FIG. 6 is a flowchart of a method, in accordance with various aspects of the present disclosure.

Each of the first and second implantable leads 120, 122 includes a flexible lead body, a plurality of conductor wires, a plurality of electrodes, and a terminal connector assembly (as shown in detail, for example, with reference to FIGS. 5-6). For example, as shown, the first implantable lead 120 includes a flexible lead body 130 having a proximal end 132, a distal end portion 134, and a plurality of conductor lumens 136 extending axially within the lead body 130 from the proximal end 132 to the distal end portion 134. The first implantable lead 120 also includes a plurality of conductor wires 138, each conductor wire extending within one of the conductor lumens 136 in the lead body 130. The first implantable lead 120 further includes a plurality of electrodes 140 coupled to the distal end portion 134 of the lead body 130. Each of the electrodes 140 are electrically coupled to at least one of the plurality of conductor wires 138. The first implantable lead 120 also includes a terminal connector assembly 142 (or terminal pin) coupled to the proximal end 132 of the lead body 130. The terminal connector assembly 142 is sized to be inserted into and received by the first connector port 110 of the header 108.

Similarly, the second implantable lead 122 includes a flexible lead body 150 having a proximal end 152, a distal end portion 154, and a plurality of conductor lumens 156 extending axially within the lead body 150 from the proximal end 152 to the distal end portion 154. The second implantable lead 122 also includes a plurality of conductor wires 158, each conductor wire extending within one of the conductor lumens 156 in the lead body 150. Further, the second implantable lead 122 includes a plurality of electrodes 160 coupled to the distal end portion 154 of the lead body 150. Each of the electrodes 160 are electrically coupled to at least one of the plurality of conductor wires 158. The second implantable lead 122 also includes a terminal connector assembly 162 coupled to the proximal end 152 of the lead body 150. The terminal connector assembly 162 is sized to be inserted into and received by the second connector port 112 of the header 108.

As an example of implant locations for one or more leads, the first implantable lead 120 is shown extending into a right ventricle of the heart, and the second implantable lead 122 extending through the coronary sinus and into a coronary vein disposed outside the left ventricle of the heart. The electrical signals and stimuli conveyed by the IMD 104 are carried to the electrode at the distal end of the lead by the conductors. The IMD 104 is typically implanted subcutaneously within an implantation location or pocket in the patient's chest or abdomen.

The IMD 104 and lead(s) 120, 122 are connected by a physician. In order to maintain the implantable leads 120, 122 connected to the IMD 104, the header 108 may include a mechanism (e.g., a collet assembly) that secures the lead(s) 120, 122 in place. As used herein, a collet assembly can refer to a number of subsystems such as a ball, roller, and/or cam with a basing member. A number of balls, rollers, and/or cams can be captured in a collet and a biasing member may engage the collet to ensure location accuracy of the collet assembly. In a first example, the collet assembly can generally act as a container for the balls, rollers, and/or cams. In a second example, the collet assembly can be one or more collets and can have a friction bias between the implantable leads 120, 122 and the one or more collets. In this way, a higher friction exists between the implantable leads 120, 122 and the one or more collets than between the housing and the one or more collets. This friction bias can be achieved by one or more methods, including but not limited to surface topology optimization, coatings, or having a roller, ball, and/or cam between the collet and housing. As used hereinafter, collet assembly may refer to any of the aforementioned examples, including the first and second examples. In addition, the securement mechanism may be releasable, in certain instances, to allow for manipulation or replacement of the lead(s) 120, 122. The securement mechanism may lessen the ability for the lead(s) 120, 122 to be removed or back out of the header 108, without intentional intervention by the physician, after the lead(s) 120, 122 have been connected. Further yet, the securement mechanism does not require any additional tool or tooling (e.g., a set screw) for connection of the lead(s) 120, 122 to the header 108.

Figure 2:
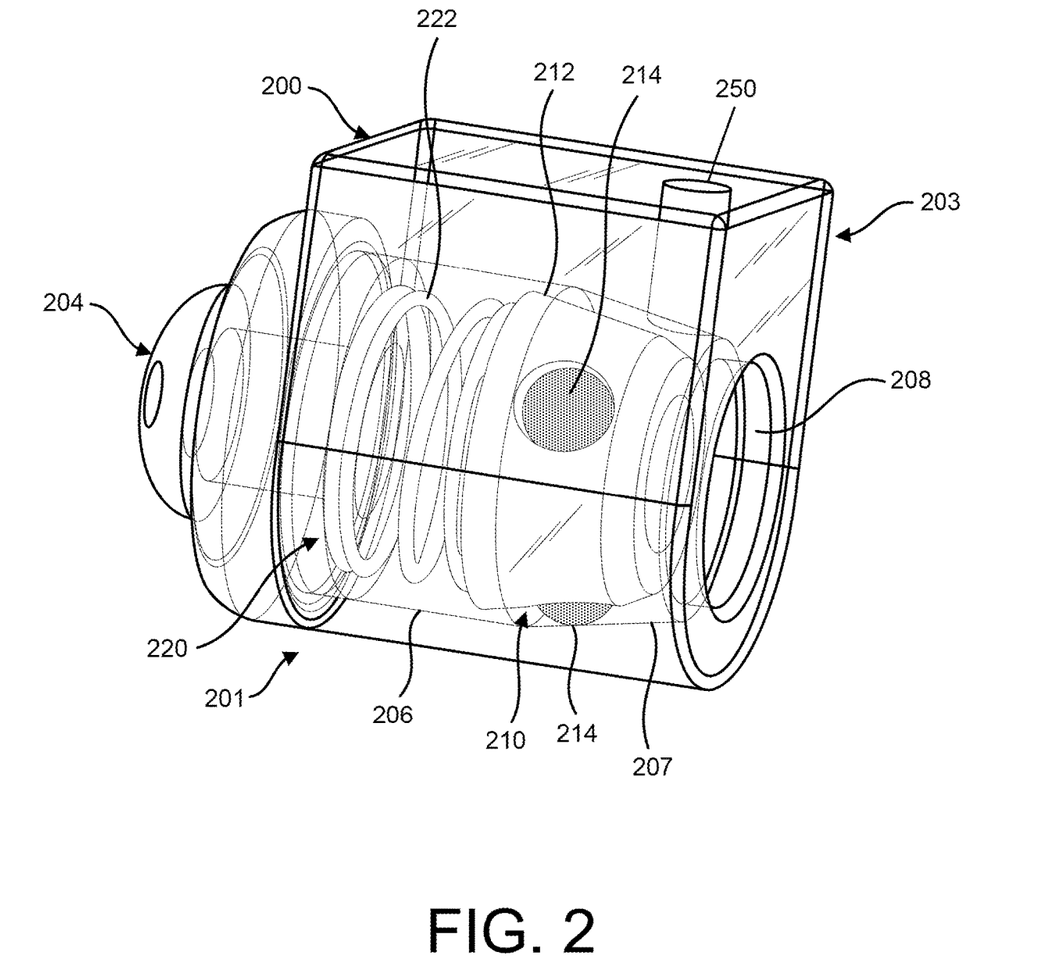
FIG. 2 is a perspective view of an illustration of an example connector port and collet assembly, in accordance with various aspects of the present disclosure.

FIG. 2 is a perspective view of an illustration of an example connector port 200 and collet assembly 210, in accordance with various aspects of the present disclosure. The connector port 200 may be arranged within a header that forms a portion of a housing of an implantable medical device as shown above with reference to FIG. 1. The connector port 200, arranged within the header, is configured to couple an implantable lead to the header (and to the implantable medical device).

In certain instances, the collet assembly 210 may include an angled outer circumference 212, and an inner surface 206 of the connector port 200 may include an angled inner circumference 207. In some examples, at least one of the angled outer circumference 212 and the angled inner circumference 207 can extend along the entire circumference of the collet assembly 210 and inner surface 206 respectively or can extend along one or more partial portions thereof. This arrangement may be advantageous in the collet assembly 210 securing the implantable lead in the connector port 200 by, for example, maintaining compressive forces on a portion of the implantable lead. In certain instances, the connector port 200 may include a proximal end 132 and a distal end 201 with the collet assembly 210 being arranged between the proximal end 132 and the distal end 201 of the connector port 200.

With inclusion of one or more bearings 214, the collet assembly 210 may move or translate within the connector port 200. In certain instances, the collet assembly 210 may include one or more bearings 214 arranged about a circumference of the collet assembly 210. The one or more bearings 214 may be configured to contact an inner surface 206 of the connector port 200. In certain instances, the one or more bearings 214 may include three or more bearings 214. The collet assembly 210 having multiple bearings 214 may centrally or symmetrically align the collet assembly 210 within the connector port 200. The one or more bearings 214 may take a variety of forms, such as a bearing ball or a rolling needle. Any number (e.g., one, two, three, etc.) or size of bearings 214 discussed herein should not be interpreted to limit the number of bearings 214 that may be included in the present disclosure. There may be an odd number of bearings 214 in some instances while in other instances there may be an even number of bearings 214. The one or more bearings 214 may facilitate movement of the collet assembly 210 within the connector port 200. The collet assembly 210 may only be held in position or constrained in the direction opposite to a direction of insertion of the implantable lead. Under these circumstances, the collet assembly 210 may otherwise be free to rotate, axially translate, or radially translate within the connector assembly, within tolerances.

In any of these examples, the one or more bearings 214 may allow the collet assembly 210 to be movable within the connector port 200 such that the one or more bearings 214 may translate toward or away from a distal end 201 of the connector port 200 in response to insertion of a portion of an implantable lead within the connector port 200.

A portion (e.g., a terminal pin) of the implantable lead may be inserted into the connector port 200 at an opening 208 therein by movement in a direction from the proximal end 132 to the distal end 201. Under these circumstances, a portion of the implantable lead that is inserted into the connector port 200 may be received and frictionally engaged by the collet assembly 210. During insertion, the one or more bearings 214 may translate along the implantable lead as the implantable lead is progressively received within the collet assembly 210 (e.g., up until a distal end of the implantable lead contacts the distal end 201 of the connector port 200). As such, the portion of the implantable lead may engage the one or more bearings 214 of the collet assembly 210. When engaged, the one or more bearings 214 may cause the collet assembly 210 to inhibit movement of the portion of the implantable lead in one or more directions relative to the collet assembly 210. The one or more bearings 214 may inhibit axial movement of the implantable lead within the collet assembly 210 in at least one direction such that the portion of the implantable lead is secured within the connector port 200. The one or more bearings 214 of the collet assembly 210 may be configured to maintain the portion of the implantable lead within the connector port 200 in response to forces acting on the implantable lead in a direction generally from the distal end 201 toward the proximal end 203. After insertion, the implantable lead is removably secured within the connector port 200.

In certain instances, the one or more bearings 214 may frictionally engage the portion of the implantable lead after insertion into the connector port 200 and the angled inner circumference 207 of the connector port 200. When the one or more bearings 214 frictionally engage the portion of the implantable lead, the one or more bearings 214 may cause the collet assembly 210 to move in the same direction (the direction of insertion of the portion of the implantable lead into the connector port 200). The one or more bearings 214 reduce the friction between the implantable lead and the collet while maintaining contact with the portion of implantable lead. During insertion, the implantable lead may move further distally than the collet assembly 210. In certain instances, the one or more bearings 214 may translate toward a distal end 201 of the connector port 200 in response to insertion of the portion of the implantable lead into the connector port 200. After insertion, the one or more bearings 214 may translate away from the distal end 201 of the connector port 200. In response to insertion, the angled inner circumference 207 of the connector port 200 can facilitate movement of the collet assembly 210 toward the proximal end 132 of the connector port 200 as the one or more bearings 214 engage the angled inner circumference 207 thereby exerting compressive or radially inward forces on the portion the implantable lead arranged within the collet assembly 210.

Arrangement of the one or more bearings 214 about the collet assembly 210 may take numerous forms. For example, arrangement of the one or more bearings 214 may be varied circumferentially, axially, and radially. In certain instances, the one or more bearings 214 may include a plurality of bearings 214. The plurality of bearings 214 may be spaced equally about the circumference of the collet assembly 210. In another instance, the plurality of bearings 214 may be spaced variedly about the circumference of the collet assembly 210. With regards to axial arrangements, each bearing in the plurality of bearings 214 may be arranged in plane with each other, for example, at a plane extending through a circumference of the collet assembly 210. In other instances, a number (e.g., one, two, three, etc.) of bearings 214 in the plurality of bearings 214 may be out of plane with the other (e.g., one, two, three, etc.) bearings 214 in the plurality of bearings 214. With regards to radial arrangements, similarly, each bearing in the plurality of bearings 214 may be equally radially spaced from a central axis of the collet assembly 210 or, on the other hand, may be variedly radially spaced from a central axis of the collet assembly 210. In any of these examples, the one or more bearings 214 may be arranged such that they do not detrimentally contact certain features of the connector port 200 (e.g., an access hole 250 for removing the implantable leads as discussed further hereinafter).

As noted above and in certain instances, the one or more bearings 214 may be forced against the portion of the implantable lead and a portion of an inner surface 206 of the connector port 200 such as the angled inner circumference 207 along which the one or more bearings 214 may translate. In this way, as the one or more bearings 214 are forced in a direction from a distal end 201 of the connector port 200 to a proximal end 132 of the connector port 200, the one or more bearings 214 may forcibly engage or collapse toward and engage the portion of the implantable lead. In certain instances, the one or more bearings 214 may be configured to contact the portion of the implantable lead and the inner surface 206 of the connector port 200 with substantially equal forces. In certain instances, the one or more bearings 214 may maintain compressive forces acting on the portion of the implantable lead in response to the forces acting on the implantable lead in a direction generally from the distal end 201 toward the proximal end 203. Under these circumstances, a magnitude of the compressive forces may be proportional to a magnitude of the forces acting on the implantable lead in a direction generally from the distal end 201 toward the proximal end 203.

In certain instances, the collet assembly 210 may be biased toward one end of the connector port 200. The collet assembly 210 may be biased toward the proximal end 203 of the connector port 200. In this manner, a location of the collet assembly 210, prior to the portion of the implantable lead being inserted into the collet assembly 210, may be maintained near or adjacent to the proximal end 203 of the connector port 200. In other instances, the collet assembly 210 may be positioned closer the distal end 201 of the connector port 200 than the proximal end 203 of the connector port 200.

A biasing member 220 may bias the collet assembly 210 in the connector port 200. The biasing member 220 may be a spring 222 (e.g., a coiled axial or torsional spring 222), a washer (e.g., planar or split), and the like, and may include any number of biasing members. For example, and in certain instances, the biasing member 220 may be a spring 222 arranged at or adjacent to the distal end 201 of the connector port 200 (e.g., between the collet assembly 210 and the end cap 204). The spring 222 may be configured to bias the collet assembly 210 toward the proximal end 203 of the connector port 200. The spring 222 may maintain a position of the collet assembly 210 and oppose the insertion force of the portion of the implantable lead into the collet assembly 210. The spring 222 may force the collet assembly 210, and more particularly the one or more bearings 214 of the collet assembly 210, to engage with the angled inner circumference 207 of the connector port 200 such that the collet assembly 210 collapses against and secures the portion of the implantable lead within the collet assembly 210.

The spring 222 may maintain engagement between the one or more bearings 214 of the collet assembly 210 and the angled inner circumference 207 of the connector port 200 to releasably secure the portion of the implantable lead within the collet assembly 210. The portion of the implantable lead may be released by moving the collet assembly 210 toward the distal end 201 of the connector port 200 (e.g., by using a tool as described further hereinafter). The spring 222 may only compress as much as required to maintain at least a portion of the collet assembly 210 proximal to the proximal end 203 of the connector port 200 during insertion. As such, when force is removed from the implantable lead after insertion, the spring 222 may again cause the one or more bearings 214 of the collet assembly 210 to engage with the angled inner circumference 207 of the connector port 200.

As noted above, the collet assembly 210 may be configured to remove pressure from the implantable lead in response to a tool moving the collet assembly 210 toward a distal end 201 of the connector port 200 through an opening 208 in the connector port 200. As the tool moves the collet assembly 210 in this way, the collet assembly 210 may open or release forces on the portion of the implantable lead to allow the portion of the implantable lead to be removed. In examples, the tool may be a component that is configured to cause the collet assembly 210 to move toward the distal end 201 of the connector port 200. The tool may be an external tool (e.g., a probe) or an internal tool (e.g., an actuator such as a button with a mounted probe or molded piece) and may be configured to removable engage the collet assembly 210 (e.g., at a tip of the probe) through an access hole 250. For example, as discussed further hereinafter, the probe may have a profiled tip (e.g., rounded, flat, etc.) configured to engage a portion of the collet assembly 210.

Figure 3:
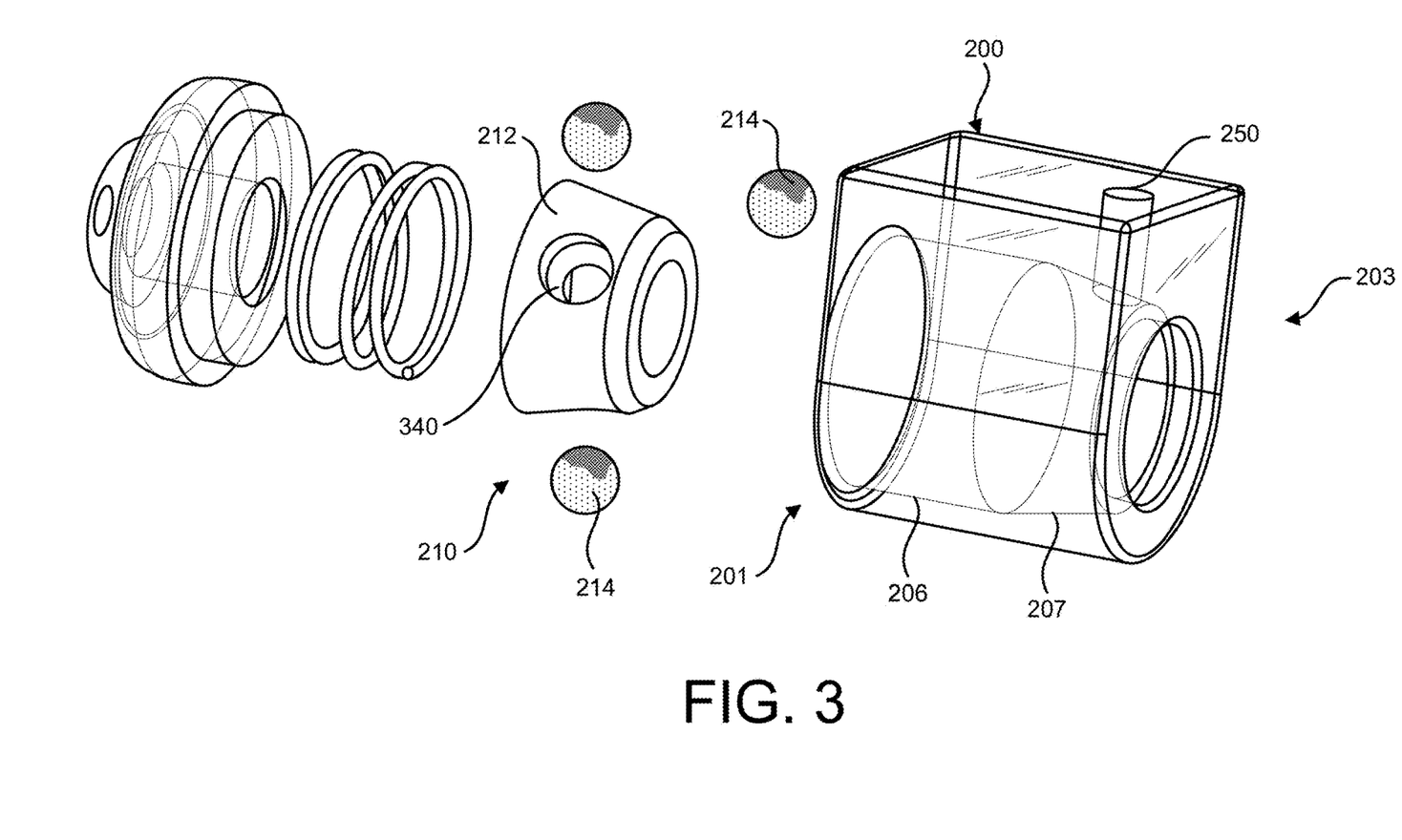
FIG. 3 is a perspective exploded view of an illustration of an example connector port and collet assembly, in accordance with various aspects of the present disclosure.

FIG. 3 is a perspective exploded view of an illustration of an example connector port and collet assembly 210, in accordance with various aspects of the present disclosure. As with previously discussed examples, the IMD shown here may include a housing, a header arranged with the housing, a connector port 200, and a collet assembly 210. The connector port 200 may be arranged within the header and configured to couple an implantable lead to the header. The collet assembly 210 may be arranged within the connector port 200 and may include one or more bearings 214 arranged about a circumference of the collet assembly 210. When the collet assembly 210 includes one or more bearings 214 arranged about a circumference of the collet assembly 210, as shown here, the one or more bearings 214 may be configured to contact an inner surface 206 of the connector port 200 arranged within the connector port 200 and configured to frictionally engage a portion of the implantable lead and to secure the implantable lead with the header in response to insertion of the portion of the implantable lead into the connector port 200.

In this example, as can be seen, the one or more bearings 214 may be configured to contact both the inner surface 206 of the connector port 200 and the implantable lead. Both a cross section of the angled outer circumference 212 of the collet assembly 210 and a cross section of the angled inner circumference 207 of the connector port 200 are tapered in a direction from a distal end 201 of the collet assembly 210 to a proximal end 203 of the collet assembly 210. In certain instances, the angle is between approximately 0.5 degrees and approximately 35 degrees. In contacting the implantable lead, some or each of the bearings 214 in the one or more bearings 214 may protrude through both ends of a bearing aperture 340 corresponding thereto. The bearing aperture(s) 340 are configured to house the each of the bearings 214 when the connector port 200 is assembled. In certain instances, some or each of the bearings 214 in the one or more bearings 214 may protrude through the aperture such that the one or more bearings 214 are allowed to further protrude into an inner-surface end of the aperture with force applied generally in the radially inward direction of the collet. Under these circumstances, the collet assembly 210 may be arranged within the connector port 200 and configured to cause the one or more bearings 214 to clamp against a portion of the implantable lead and to secure the implantable lead with the header in response to insertion of the portion of the implantable lead into the connector port 200. Such a sequence (and similar sequences discussed herein) may be characterized as automatically locking the implantable lead to the connector port 200.

The IMD may inhibit release of the implantable lead once the portion of the implantable lead is arranged within the collet assembly 210 or by pulling the implantable lead out of the connector port 200. The collet assembly 210 may exert forces on the portion of the implantable lead that is frictionally engaged with the one or more bearings 214. As noted above, the one or more bearings 214 may maintain compressive forces acting on the portion of the implantable lead in response to the forces acting on the implantable lead in a direction generally from the distal end 201 toward the proximal end 203. In certain instances, the one or more bearings 214 may secure the implantable lead with the header such that the implantable lead is secured with the header when the one or more bearings 214 translate toward a proximal end 203 of the connector port 200 in response to forces acting opposite to those of insertion of the implantable lead into the connector port 200 (e.g., pulling forces). Under these circumstances, the one or more bearings 214 may maintain compressive forces on the implantable lead that are proportional to the forces acting on the implantable lead in a direction generally from the distal end 201 toward the proximal end 203. For example, increased pulling forces will result in proportionally increased clamping forces to ensure that the implantable lead stays secured to the connector port 200. In this way, unintentional removal of the implantable lead may be limited.

Release of the implantable lead may require a tool or additional intervention. In certain instances, a proximal end of the angled outer circumference 212 may be configured to accommodate engagement of a probe to release the implantable lead from the collet assembly 210 as discussed further elsewhere herein. For example, the proximal end of the angled outer circumference 212 may be chamfered or beveled such that the chamfer or bevel are aligned with the access hole 250 through which the probe may protrude to engage the angled outer surface. In this way, axial motion of the collet assembly 210 toward the distal end 201 of the connector port 200 may by way of radially inward motion of the probe (e.g., in a downward direction radially inward of the outer circumferential surface) may be facilitated by contacting the chamfer or bevel with the probe. It should be noted that the probe may have a matching chamfer or bevel at the tip thereof or may be a blunt, rounded, or standard tip while maintaining similar operation. The probe may also operate by levering or otherwise causing the collet to move toward the distal end 201 of the connector port 200. In addition, or in alternative, the implantable lead may be released via a torque release mechanism. In examples, a torque release mechanism may be a cam configured to connector port 200 such that access with a tool through 250 would facilitate rotation of the cam, pushing collet 210 toward the distal end 201. In other examples, the torque release mechanism may be similar to the aforementioned tool, such as a torque wrench, a molded-in-place button or pin assembly, forceps, or any other mechanism that can cause the collet assembly to move toward the distal end 201 of the connector port 200.

Figure 4:
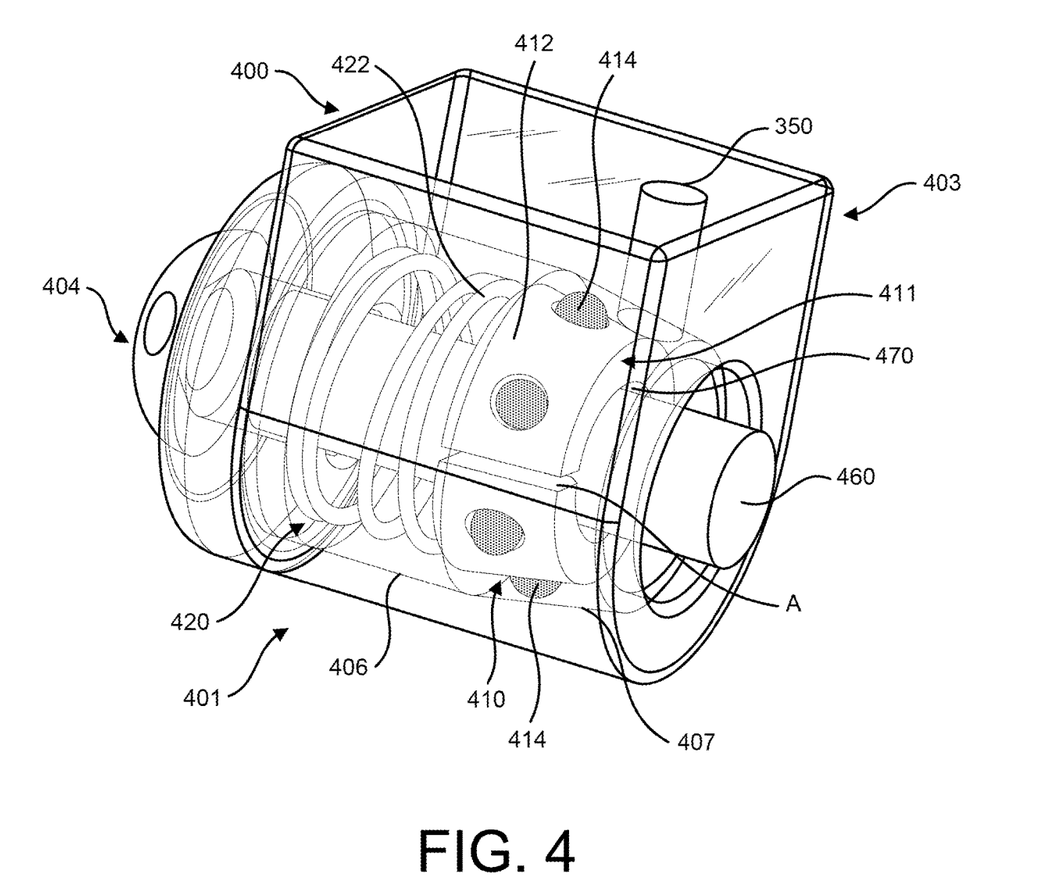
FIG. 4 is a perspective view of an illustration of another example connector port and collet assembly, in accordance with various aspects of the present disclosure.

FIG. 4 is a perspective view of an illustration of another example connector port 400 and collet assembly 410, in accordance with various aspects of the present disclosure. The connector port 400 may be arranged within a header that forms a portion of a housing of an implantable medical device as shown above with reference to FIG. 1. Like the connector port 200, the connector port 400, arranged within the header, is configured to couple an implantable lead 460 to the header (and to the implantable medical device). In certain instances, the connector port 400 may include an end cap 404. Like the collet assembly 210, the collet assembly 410 may be arranged within the connector port and may be configured to frictionally engage a portion of the implantable lead 460 and secure the implantable with the header in response to insertion of the portion of the implantable lead 460 into the connector port.

The collet assembly 410 may resemble those collet assemblies discussed elsewhere herein. For example, the collet assembly 410 shown here includes an angled outer circumference 412 and an inner surface 406 of the connector port 400 includes an angled inner circumference 407. Each of the angled outer circumference 412 and the angled inner circumference 407 may have an angle that is approximately the same as the other. Both a cross section of the angled outer circumference 412 of the collet assembly 410 and a cross section of the angled inner circumference 407 of the connector port 400 are tapered in a direction from a distal end of the collet assembly 410 to a proximal end of the collet assembly 410. The angle may be between approximately 0.5 degrees and approximately 35 degrees. As with previously discussed examples, geometry of the connector port 400 and the collet assembly 410 may facilitate the collet assembly 410 frictionally engaging and securing the implantable lead 460 with the header. And such an arrangement may be advantageous in the collet assembly 410 securing the implantable lead 460 in the connector port 400 (e.g., by maintaining compressive forces on a portion of the implantable lead 460). The connector port 400 may include a proximal end 403 and a distal end 401 with the collet assembly 410 being arranged between the proximal end 403 and the distal end 401 of the connector port 400.

As with previous example, this example of the collet assembly 410 may include one or more bearings 414 arranged about a circumference of the collet assembly 410 and configured to contact an inner surface 406 of the connector port 400. The one or more bearings 414 translate toward a distal end 401 of the connector port 400 in response to insertion of the portion of the implantable lead 460 into the connector port 400. The one or more bearings 414 include a plurality of bearings 414 spaced equally about the circumference of the collet assembly 410. In contacting the inner surface 406 of the connector port 400 during operation, these bearings 414 may exert forces on the implantable lead 460. The one or more bearings 414 of the collet assembly 410 may be configured to maintain the portion of the implantable lead 460 within the connector port 400 in response to forces acting on the implantable lead 460 in a direction generally from the distal end 401 toward the proximal end 403. The one or more bearings 414 maintain compressive forces acting on the portion of the implantable lead 460 in response to the forces acting on the implantable lead 460 in a direction generally from the distal end 401 toward the proximal end 403.

With this example, the combination of the one or more bearings 414 and a split construction of the collet assembly 410 may allow the collet assembly 410 (e.g., in addition to or instead of the one or more bearings 414) to frictionally engage the implantable lead 460. In certain instances, the collet assembly 410 may be configured to clamp down on the portion of the implantable lead 460 in response to insertion of the portion of the implantable lead 460 into the connector port 400. In this case, the one or more bearings 414 reduce the friction between the connector port 400 and the collet. In certain instances, the collet assembly 410 may be split 480 at a portion of a circumference thereof. In certain instances, the collet assembly 410 may be split at more than one portion of a circumference thereof. In any of these instances, the split 480 may be configured to open and close to thereby allow the inner diameter of the collet assembly 410 to change (e.g., increase or decrease) within limits. In this way, the collet assembly may comprise either a single collet or a multiple-member collet that clamps down on the portion of the implantable lead 460 and may have a friction imbalance such that a higher friction exists between the implantable leads 460 and the collet assembly 410 than between the connector port 400 and the collet assembly 410. For example, the collet assembly 410 may have a first inner diameter when in a resting position and may have a second inner diameter that is smaller than the first inner diameter as the collet assembly experiences compressive forces. As the split 480 closes, an inner surface 470 a collet 411 of the collet assembly 410 may be brought into contact or into further contact with the implantable lead 460.

In certain instances, the collet assembly 410 includes an angled outer circumference 412 and an inner surface 406 of the connector port 400 includes an angled inner circumference 407. An angle of the angled outer circumference 412 of the collet assembly 410 may be approximately equal to an angle of the angled inner circumference 407 of the connector port 400. In this way, the angled outer circumference 412 and the angled inner circumference 407 may be complementary such that movement of the collet assembly 410 between the proximal and distal ends of the connector port 400 may be free from interference at certain points. And at other points (e.g., when the one or more bearings 414 translate along the angled inner circumference), movement of the collet assembly 410 between the proximal and distal ends of the connector port 400 may correspondingly cause the collet assembly 410 to experience compressive forces. Under these circumstances, the split may correspondingly open as the one or more bearings 414 translate along the angled inner surface toward the distal end of the connector port 400 and close as the one or more bearings 414 translate along the angled inner surface toward the proximal end 403 of the connector port 400.

The collet assembly 410 may be biasedly arranged (e.g., via a biasing member 420) within the connector port 400 as with previously-discussed examples. In certain instances, the connector port 400 may include a proximal end 403 and a distal end with the collet assembly 410 being arranged between the proximal end 403 and the distal end of the connector port 400 and the collet assembly 410 biased toward the proximal end 403 of the connector port 400. The collet assembly 410 may be positioned closer the proximal end 403 of the connector port 400 than the distal end of the connector port 400. In certain instances, the IMD may include a biasing member 420 in the form of a spring 422 arranged at the distal end of the connector port 400 configured to bias the collet assembly 410 toward the proximal end 403 of the connector port 400. As with examples previously discussed herein, releasing the implantable lead 460 from the collet assembly 410 may require a tool. For example, releasing the implantable lead 460 may require moving the collet assembly 410 toward the distal end of the connector port 400 relative to the implantable lead 460. In certain instances, the collet assembly 410 may be configured to remove pressure from the implantable lead 460 in response to a tool moving the collet assembly 410 toward a distal end of the connector port 400 through an opening 350 in the connector port 400. In addition, or in alternative, the implantable lead 460 may be released via a torque release mechanism.

FIG. 5 is a perspective exploded view of an illustration of another example connector port and collet assembly 410, in accordance with various aspects of the present disclosure. As with the previous example, the connector port may be arranged within a header that forms a portion of a housing of an implantable medical device as shown above with reference to FIG. 1. The connector port, arranged within the header, is configured to couple an implantable lead 460 to the header (and to the implantable medical device). The collet assembly 410 may be arranged within the connector port and may be configured to clamp against a portion of the implantable lead 460 and to secure the implantable with the header in response to insertion of the portion of the implantable lead 460 into the connector port.

As discussed in detail above, in this example, the one or more bearings 414 may be configured to contact both the inner surface of the connector port and the implantable lead 460. The collet assembly 410, as opposed to the bearings 414, clamps against the implantable lead 460 to secure the implantable lead 460 to the connector port. As noted prior, both a cross section of the angled outer circumference of the collet assembly 410 and a cross section of the angled inner circumference of the connector port are tapered in a direction from a distal end of the collet assembly 410 to a proximal end of the collet assembly 410. The angle may be between approximately 0.5 degrees and approximately 35 degrees. In contacting the implantable lead 460, some or each of the bearings 414 in the one or more bearings 414 may protrude through both ends of a bearing aperture corresponding thereto and being configured to house the bearing when the connector port is assembled.

FIG. 6 is a flowchart of a method 600, in accordance with various aspects of the present disclosure. As shown here, the present disclosure includes a method 600 of coupling an implantable lead to an implantable medical device. The method 600 may include coupling the implantable lead to the implantable medical device by moving the implantable lead in a first direction into a connector port arranged within a header of the implantable medical device at step 602. At steps 604 and 606, the method 600 may include engaging and securing a portion of the implantable lead with a collet assembly arranged within the connector port in response to insertion of the portion of the implantable lead into the connector port. In certain instances, engaging and securing the portion of the implantable lead may include clamping the collet assembly on the portion of the implantable lead in response to insertion of the portion of the implantable lead into the connector port. In certain instances, engaging and securing the portion of the implantable lead includes forcing one or more bearings of the collet assembly against the portion of the implantable lead and a portion of an inner surface of the connector port.

While shown here as discrete steps, each step of the method can be performed simultaneously or substantially simultaneously with one or more other steps. As noted elsewhere herein, the method may include automatically securing the implantable lead such that, for example, both engaging a portion of the implantable lead with a collet assembly at step 604 and securing a portion of the implantable lead with the collet assembly at step 606 can be performed simultaneously or substantially simultaneously. In this way, other than moving the implantable lead in a first direction into a connector port at step 602, no additional user intervention is required to secure the implantable lead with the collet assembly.

Aspects of the present disclosure, including those discussed in relation to FIGS. 2-6, provide numerous advantages. For example, typical applications of a connector port employ a combination of a tip block, a set screw, and a torque wrench to secure and release an implantable lead. By removing these components, the present disclosure reduces the amount of noise issues in the field from no or under torqued set screws. In addition, usability is improved because the present disclosure allows for easy attachment of the implantable lead and because relative axial motion of the lead within the connector port may be inhibited. As well, the overall design of the IMD may be improved because the need for certain components (e.g., top mounted seal plugs) may be eliminated. By simplifying the design of the retaining mechanism and eliminating certain components, the profile of the header may also be improved. Plus, the associated manufacturing process may be simple.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device comprising:
   a housing;

a header arranged with the housing;
a connector port arranged within the header and configured to couple an implantable lead to the header, the connector port including a proximal end, an opposite distal end, and an access hole extending radially through the connector port between the proximal and distal ends of the connector port; and
a collet assembly arranged within the connector port and configured to clamp against a portion of the implantable lead and to secure the implantable lead with the header in response to insertion of the portion of the implantable lead into the connector port,
wherein the access hole is aligned with the proximal end of the collet assembly and is configured to receive a tool for engaging the proximal end of the collet assembly to cause the collet assembly to move in an axial direction toward the distal end of the connector port.

2. The implantable medical device of claim 1, wherein the collet assembly includes one or more bearings arranged about a circumference of the collet assembly and configured to contact an inner surface of the connector port.

3. The implantable medical device of claim 2, wherein the one or more bearings translate toward a distal end of the connector port in response to insertion of the portion of the implantable lead into the connector port.

4. The implantable medical device of claim 3, wherein the one or more bearings include a plurality of bearings spaced equally about the circumference of the collet assembly.

5. The implantable medical device of claim 1, wherein the collet assembly is split at a portion of a circumference thereof.

6. The implantable medical device of claim 1, wherein the collet assembly includes an angled outer circumference and an inner surface of the connector port includes an angled inner circumference.

7. The implantable medical device of claim 6, wherein an angle of the angled outer circumference of the collet assembly is approximately equal to an angle of the angled inner circumference of the connector port.

8. The implantable medical device of claim 7, wherein both a cross section of the angled outer circumference of the collet assembly and a cross section of the angled inner circumference of the connector port are tapered in a direction from a distal end of the collet assembly to a proximal end of the collet assembly, and wherein the angle is between approximately 0.5 degrees and approximately 35 degrees.

9. An implantable medical device comprising:
a housing;
a header arranged with the housing;
a connector port arranged within the header and configured to couple an implantable lead to the header, the connector port including a proximal end, an opposite distal end, and an access hole extending radially through the connector port between the proximal and distal ends of the connector port; and
a collet assembly including one or more bearings arranged about a circumference of the collet assembly, the one or more bearings configured to contact an inner surface of the connector port arranged within the connector port and configured to frictionally engage a portion of the implantable lead and to secure the implantable lead with the header in response to insertion of the portion of the implantable lead into the connector port,
wherein the access hole is aligned with the proximal end of the collet assembly and is configured to receive a tool for engaging the proximal end of the collet assembly to cause the collet assembly to move in an axial direction toward the distal end of the connector port.

10. The implantable medical device of claim 9, wherein the collet assembly or a portion thereof includes an angled outer circumference, and an inner surface of the connector port or a portion thereof includes an angled inner circumference, or both.

11. The implantable medical device of claim 9, wherein the one or more bearings translate toward a distal end of the connector port in response to insertion of the portion of the implantable lead into the connector port.

12. The implantable medical device of claim 9, wherein the one or more bearings include a plurality of bearings spaced equally about the circumference of the collet assembly.

13. The implantable medical device of claim 9, wherein the one or more bearings are forced against the portion of the implantable lead and a portion of an inner surface of the connector port.

14. The implantable medical device of claim 13, wherein the one or more bearings are configured to contact the portion of the implantable lead and the inner surface of the connector port with substantially equal forces.

15. The implantable medical device of claim 9, wherein the one or more bearings secure the implantable lead with the header such that the implantable lead is secured with the header when the one or more bearings translate toward a proximal end of the connector port in response to forces acting opposite to those of insertion of the implantable lead into the connector port.

16. A medical method comprising:
coupling an implantable lead to an implantable medical device by moving the implantable lead in a first direction into a connector port arranged within a header of the implantable medical device, the connector port including a proximal end, an opposite distal end, and an access hole extending radially through the connector port between the proximal and distal ends of the connector port;
engaging and securing a portion of the implantable lead with a collet assembly arranged within the connector port in response to insertion of the portion of the implantable lead into the connector port;
inserting a tool into the access hole in the connector port; and
engaging a proximal end of the collet assembly with the tool to cause the collet assembly to move axially toward the distal end of the connector port to release the portion of the implantable lead from the collet assembly.

17. The method of claim 16, wherein engaging and securing the portion of the implantable lead includes clamping the collet assembly on the portion of the implantable lead in response to insertion of the portion of the implantable lead into the connector port.

18. The method of claim 16, wherein the collet assembly is split at a portion of a circumference thereof.

19. The method of claim 16, wherein engaging and securing the portion of the implantable lead includes forcing one or more bearings of the collet assembly against the portion of the implantable lead and a portion of an inner surface of the connector port.

20. The method of claim 19 wherein the one or more bearings are configured to contact the portion of the implantable lead and the inner surface of the connector port with substantially equal forces.

* * * * *